United States Patent [19]

Long et al.

[11] Patent Number: 5,538,967
[45] Date of Patent: Jul. 23, 1996

[54] ARTHROPODICIDAL OXAZINES AND THIAZINES

[75] Inventors: Jeffrey K. Long, Wilmington; Thomas M. Stevenson, Newark, both of Del.

[73] Assignee: E. I. Du Pont de Nemours and Company, Wilmington, Del.

[21] Appl. No.: 374,283

[22] Filed: Jan. 18, 1995

[51] Int. Cl.$^6$ .................. A61K 31/535; C07D 265/08; C07D 279/06; C07D 413/04
[52] U.S. Cl. .................. 514/226.8; 514/228.8; 544/53; 544/54; 544/55; 544/69; 544/88; 544/96
[58] Field of Search ................. 544/53, 54, 55, 544/69, 88, 96; 514/226.8, 228.8

[56] References Cited

FOREIGN PATENT DOCUMENTS

| 0635500 | 1/1995 | European Pat. Off. ...... C07D 265/08 |
| WO94/14783 | 7/1994 | WIPO .................. C07D 265/08 |

OTHER PUBLICATIONS

Itoh et al, Chemical Abstracts 122:265391 for EP 635500 (Jan. 25, 1995).

*Primary Examiner*—Philip I. Datlow

[57] ABSTRACT

Substituted oxazines and thiazines, arthropodicidal compositions containing them and methods of controlling arthropods are provided. The oxazines and thiazines having the formula

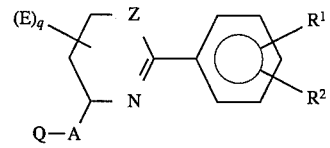

wherein Z is O or S;

Q is phenyl or pyridyl substituted with alkenyl, alkynyl or substituted phenyl; and A, E, q, $R^1$ and $R^2$ are as described.

10 Claims, No Drawings

ARTHROPODICIDAL OXAZINES AND THIAZINES

BACKGROUND OF THE INVENTION

This invention relates to certain oxazines and thiazines, including all geometric and stereoisomers, agriculturally-suitable salts thereof, agricultural compositions containing them and their use as arthropodicides in both agronomic and nonagronomic environments.

WO 94/14783 discloses pesticidal 2-phenyl-1,3-oxazine or 1,3-thiazine derivatives of the following general formula:

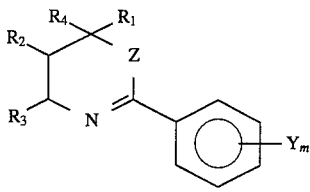

wherein:

Z is O or S;

Y is halogen, $NO_2$, CN, or optionally substituted alkyl, alkoxycarbonyl, alkoxy or amino, or $S(O)_p r^1$;

p is 0–2;

m is 1–3;

$r^1$ is optionally substituted alkyl;

$R_1$, $R_2$ and $R_4$ are H or optionally substituted alkyl or phenyl;

$R_3$ is alkyl, alkenyl, aralkyl, cycloalkyl, phenyl, naphthyl, pyridyl, furyl or thienyl, all optionally substituted by halogen, OH, alkyl, cycloalkyl, phenyl, alkoxy, phenoxy, heterocyclyl, heterocyclyloxy, alkylthio, phenylthio or amino, which may be further substituted.

The oxazines and thiazines of this invention are not disclosed in this document.

SUMMARY OF THE INVENTION

This invention comprises compounds of Formula I, including all geometric and stereoisomers, agriculturally-suitable salts thereof, agricultural compositions containing them and their use as arthropodicides in both agronomic and nonagronomic environments:

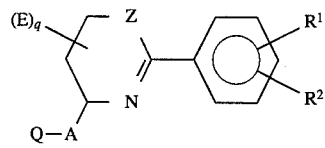

wherein:

A is selected from the group direct bond, $C_1$–$C_3$ alkylene and $C_2$–$C_4$ alkenylene;

Q is selected from the group phenyl, pyridyl, thienyl, furyl and naphthyl, each ring substituted with $R^3$, $R^4$ and $R^5$;

E is selected from the group $C_1$–$C_4$ alkyl and $C_1$–$C_4$ haloalkyl;

Z is selected from the group O and S;

$R^1$ and $R^2$ are independently selected from the group H, halogen, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, CN and $NO_2$;

$R^3$ is selected from the group $C_1$–$C_{10}$ alkyl substituted with at least one member independently selected from the group CN, $NO_2$, $Si(R^6)(R^7)(R^8)$, $C_2$–$C_6$ alkylcarbonyl, $C_2$–$C_6$ haloalkylcarbonyl, $C_2$–$C_6$ alkoxycarbonyl, and $C_2$–$C_6$ haloalkoxycarbonyl; $C_2$–$C_6$ alkylcarbonyl; $C_2$–$C_6$ haloalkylcarbonyl; $C_2$–$C_6$ alkoxycarbonyl; $C_2$–$C_6$ haloalkoxycarbonyl; $C_2$–$C_{10}$ alkenyl optionally substituted with at least one member independently selected from $R^9$; $C_2$–$C_{10}$ alkynyl optionally substituted with at least one member independently selected from $R^9$; $C(O)R^{14}$; $C(O)OR^{14}$; $C(O)N(R^{10})R^{11}$; $OR^{12}$; —$C(R^{10})$=N— $OR^{11}$; —O—N=$C(R^{10})(R^{11})$; phenyl substituted with at least one member independently selected from $W^1$; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^4$ and $R^5$ are independently selected from the group H, halogen, CN, $NO_2$, $C_1$–$C_{16}$ alkyl, $C_1$–$C_{16}$ alkoxy, $C_1$–$C_{16}$ haloalkyl, $C_1$–$C_{16}$ haloalkoxy, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, and phenyl optionally substituted with at least one member independently selected from W;

$R^6$ and $R^7$ are independently selected from the group $C_1$–$C_6$ alkyl;

$R^8$ is selected from the group $C_1$–$C_6$ alkyl and phenyl optionally substituted with W;

$R^9$ is selected from the group halogen, CN and $Si(R^6)(R^7)(R^8)$; or $R^9$ is selected from the group phenyl and pyridyl, each optionally substituted with at least one member independently selected from W;

$R^{10}$ and $R^{11}$ are independently selected from the group H, $C_1$–$C_6$ alkyl, $C_1$–$C_6$ haloalkyl, phenyl optionally substituted with at least one member independently selected from W, and benzyl optionally substituted with at least one member independently selected from W;

$R^{12}$ is selected from the group tetrahydropyranyl; $C_1$–$C_{10}$ alkyl substituted with at least one member independently selected from the group CN, $Si(R^6)(R^7)(R^8)$, $C_2$–$C_6$ alkylcarbonyl, $C_2$–$C_6$ haloalkylcarbonyl, $C_2$–$C_6$ alkoxycarbonyl and $C_2$–$C_6$ haloalkoxycarbonyl; $C_2$–$C_{10}$ alkenyl optionally substituted with at least one member independently selected from the group halogen, CN and $C_2$–$C_6$ alkoxycarbonyl; $C_3$–$C_7$ cycloalkyl; $C_3$–$C_7$ halocycloalkyl; $C_4$–$C_7$ cyanocycloalkyl; $C_4$–$C_7$ alkylcycloalkyl; $C_4$–$C_7$ cycloalkylalkyl; $C_4$–$C_7$ halocycloalkylalkyl; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^{13}$ is selected from the group $C_1$–$C_3$ alkyl and $C_1$–$C_3$ haloalkyl;

$R^{14}$ is selected from the group phenyl and pyridyl, each optionally substituted with at least one member independently selected from W;

W is selected from the group halogen, CN, CHO, $NO_2$, $SF_5$, $C_1$–$C_3$ alkyl, $C_1$–$C_3$ haloalkyl, $C_1$–$C_3$ alkylthio, $C_1$–$C_3$ alkoxy, $C_1$–$C_3$ haloalkoxy, $C_2$–$C_4$ alkylcarbonyl and $C_2$–$C_4$ alkoxycarbonyl;

$W^1$ is selected from the group CN, CHO, $NO_2$, $SF_5$, $S(O)_n R^{13}$, $C_2$–$C_4$ alkylcarbonyl, $C_2$–$C_4$ alkoxycarbonyl, —$C(R^{10})$=N—$OR^{11}$ and —O—N=$C(R^{10})(R^{11})$; or $W^1$ is selected from the group $C_2$–$C_4$ alkenyl, $C_2$–$C_4$ alkynyl, O—$C_2$—$C_4$ alkenyl and O—$C_2$—$C_4$ alkynyl, each group optionally substituted with $R^9$;

n is 0, 1 or 2; and q is 0, 1, 2 or 3.

Preferred Compounds A are compounds of Formula I wherein

A is a direct bond;

Q is selected from the group phenyl and pyridyl, each ring substituted with $R^3$, $R^4$ and $R^5$;

$R^1$ is selected from the group F and Cl in the 2-position;

$R^2$ is selected from the group H, F and Cl in the 6-position; and $R^3$ is selected from the group $C_2$–$C_{10}$ alkenyl optionally substituted with at least one member independently selected from $R^9$; $C_2$–$C_{10}$ alkynyl optionally substituted with at least one member independently selected from $R^9$; and phenyl substituted with at least one member independently selected from $W^1$.

Preferred Compounds B are compounds of Preferred A wherein $R^3$ is selected from the group $C_2$–$C_{10}$ alkenyl optionally substituted with at least one member independently selected from $R^9$; and $R^9$ is selected from the group phenyl and pyridyl, each optionally substituted with at least one member independently selected from W.

Preferred Compounds C are compounds of Preferred B wherein

Z is O;

$R^4$ and $R^5$ are H; and

W is selected from halogen, CN, and $OCHF_2$.

Preferred Compounds D are compounds of Preferred A wherein $R^3$ is selected from the group $C_2$–$C_{10}$ alkynyl optionally substituted with at least one member independently selected from $R^9$; and $R^9$ is selected from the group phenyl and pyridyl, each optionally substituted with at least one member independently selected from W.

Preferred Compounds E are compounds of Preferred D wherein

Z is O;

$R^4$ and $R^5$ are H; and

W is selected from halogen, CN, and $OCHF_2$.

Preferred Compounds F are compounds of Preferred A wherein $R^3$ is phenyl substituted with at least one member independently selected from $W^1$;

$W^1$ is selected from the group $C_2$–$C_4$ alkenyl and $C_2$–$C_4$ alkynyl, O—$C_2$—$C_4$ alkenyl and O—$C_2$—$C_4$ alkynyl, each group optionally substituted with $R^9$.

Specifically preferred for biological activity is Compound G of Preferred D which is:

2-(2,6-difluorophenyl)-4-[4-[(4-fluorophenyl)ethynyl]phenyl]-5,6-dihydro-4H- 1,3-oxazine.

Compounds of this invention can exist as one or more stereoisomers. The various stereoisomers include enantiomers, diastereomers and geometric isomers. One skilled in the art will appreciate that one stereoisomer may be more active than the others and how to separate stereoisomers. Accordingly, the present invention comprises racemic and optically active compound(s). The term optically active compound(s) includes individual stereoisomers, mixtures of stereoisomers enriched in one stereoisomer, and optically active mixtures of compounds.

The term "fused bicyclic ring system" is defined as those ring systems which satisfy the Hückel rule, including 8- to 12-membered fused bicyclic ring systems containing 0 to 4 heteroatoms and 1 or 2 aromatic rings, examples include naphthyl, tetralinyl, quinolyl, isoquinolyl, quinoxalinyl, benzofuryl, isobenzofuranyl, benzothienyl, benzodioxolyl, benzoxazolyl, chromanyl, indolinyl, isoindolyl, thienofuranyl, and purinyl. The aromatic ring systems can be attached through any available carbon or nitrogen, for example, for naphthyl, the bicyclic aromatic ring system is 1-naphthyl or 2-naphthyl, for benzofuryl, the aromatic ring system can be 2-, 3-, 4-, 5-, 6-, or 7-benzofuryl, and similarly for the other bicyclic ring systems.

The term "alkyl" used either alone or in compound words such as "alkylthio" or "haloalkyl", denotes straight or branched alkyl such as methyl, ethyl, n-propyl, isopropyl and the different butyl, pentyl and higher isomers. Alkoxy denotes methoxy, ethoxy, n-propyloxy, isopropyloxy and the different butoxy, pentoxy, hexyloxy and higher isomers. Alkenyl denotes straight or branched chain alkenes such as vinyl, 1-propenyl, 2-propenyl and the different butenyl, pentenyl, hexenyl and higher isomers. Alkynyl denotes straight chain or branched alkynes such as ethynyl, 1-propynyl, 2-propynyl and the different butynyl, pentynyl, hexynyl, and the higher isomers. Cycloalkyl denotes cyclopropyl, cyclobutyl, cyclopentyl, cyclohexyl and cycloheptyl. Cyanocyloalkyl denotes the carbocyclic rings above substituted by cyano. Alkylcycloalkyl denotes the above carbocyclic rings substituted with a straight or branch-chained alkyl group. Cycloalkylalkyl denotes a straight or branch-chained alkyl group substituted by cyclopropyl, cyclobutyl, cyclopentyl or cyclohexyl. Alkoxyalkoxy denotes alkoxy substitution on alkoxy. Alkylcarbonyl denotes carbonyl with an attached straight or branch-chained alkyl group. Alkoxycarbonyl denotes carbonyl with an attached straight or branch-chained alkoxy group.

The term "halogen", either alone or in compound word such as "haloalkyl", denotes fluorine, chlorine, bromine or iodine. Further, when used in compound words such as "haloalkyl", said alkyl can be partially or fully substituted with independently selected halogen atoms. Examples of haloalkyl include $CH_2CH_2F, CF_2CF_3$ and $CH_2CHFCl$. The terms "haloalkenyl", "haloalkynyl", "haloalkoxy", "haloalkylcarbonyl", "haloalkoxycarbonyl", "halocycloalkyl" and "halocycloalkylalkyl" are defined analogously to the term "haloalkyl".

The total number of carbon atoms in a substituent group is indicated by the "$C_i$–$C_j$" prefix where i and j are numbers from 1 to 16. For example, $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$.

When a compound is substituted with a substituent bearing a subscript that indicates the number of said substituents can exceed 1, said substituents (when they exceed 1) are independently selected from the group of defined substituents.

DETAILED DESCRIPTION OF THE INVENTION

The following methods may be used to prepare the compounds of this invention. Substituents are as defined in the summary unless otherwise indicated.

By carrying out the reaction of Scheme 1 in an inert solvent such as benzene, tetrahydrofuran, acetonitrile, etc., at a temperature of −20° C. to the boiling point of the solvent for 30 minutes to 48 hours and using, as desired, a dehydrogenating agent such as a dialkylazodicarboxylate, etc., and a deoxygenating agent such as triphenylphosphine, etc., a compound of Formula I having an oxygen atom for Z can be prepared. If a sulfurizing reagent such as Lawesson's reagent, phosphorus pentasulfide, etc., is used, a compound of Formula I having a sulfur atom for Z is obtained.

Scheme 1

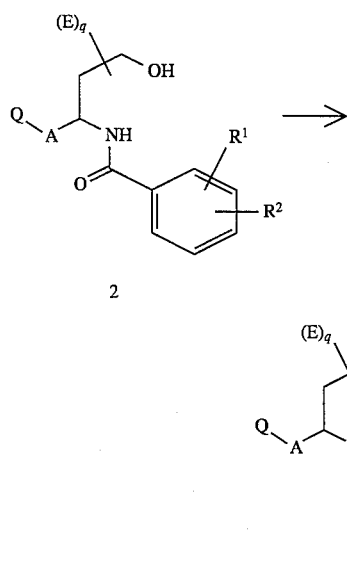

The intermediates of Formula 2 are prepared as in Scheme 2. The reaction is carried out at a temperature of −20° C. to the boiling point of an inert solvent selected from water, benzene, tetrahydrofuran, acetonitrile, dichloromethane, N,N-dimethylformamide, etc., for 30 min to five days using, as desired, an acid-binding agent such as pyridine, triethylamine, sodium hydroxide, etc., or a dehydrating agent such as concentrated sulfuric acid, dicyclohexylcarbodiimide, etc.

Scheme 2

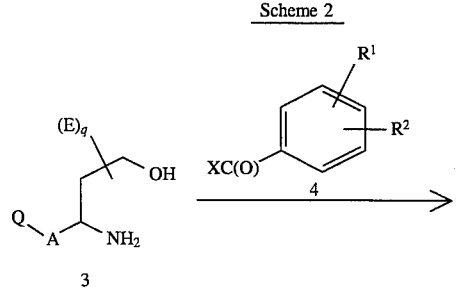

-continued
Scheme 2

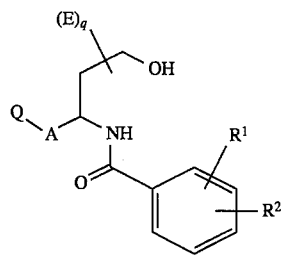

X = halogen, OH, OSO$_2$CH$_3$, imidazolyl, OSO$_2$(C$_6$H$_4$)CH$_3$

The acylating agents 4 of Scheme 2 are benzoic acid derivatives and are commercially available or are readily available by procedures well known in the art. The 1,3-aminoalcohols 3 are prepared by literature procedures (e.g., P. G. Gassman, et al, *Tetrahedron Lett.* (1985), 26 (41), 4971–74; P. A. Wade, el. al., *Tetrahedron Lett.* (1989), 30 (44), 5969; U. Schoellkopf, et. al., *Angew. Chem.* (1973), 85, 355).

Alternatively, compounds 2 are prepared as in Scheme 3. The reaction is carried out at −20° C. to the boiling point of an inert solvent selected from tetrahydrofuran, ethyl ether, hexane, toluene, etc., for 30 min to 72 h using a borane or borane complex followed by oxidative work-up with, for example, aqueous peroxide and base, or other methods as known in the art (e.g., H. C. Brown, et al, *J. Amer. Chem. Soc.* (1968), 90, 5280).

Scheme 3

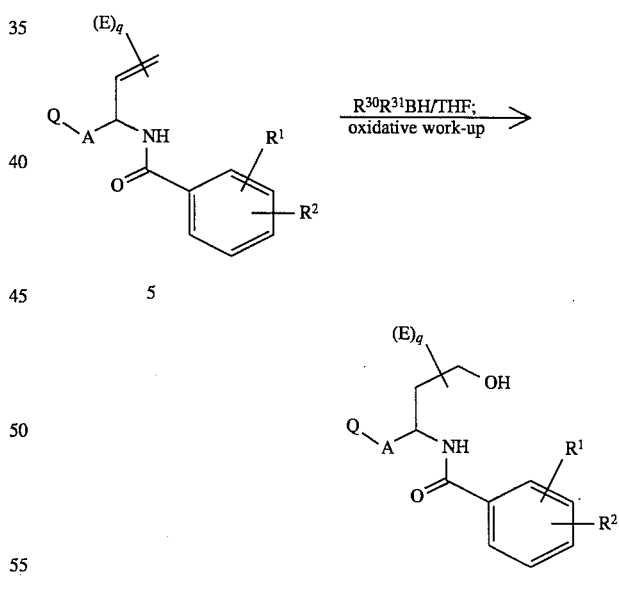

R$^{30}$ and R$^{31}$ = H, (substituted) alkyl, etc., as per the known art of hydroboration chemistry The compounds 5 are prepared as in Scheme 4. The reaction is carried out at a temperature of −20° C. to the boiling point of an inert solvent selected from water, benzene, tetrahydrofuran, acetonitrile, dichloromethane, N,N-dimethylformamide, etc., for 30 min to five days using, as desired, an acid-binding agent such as pyridine, triethylamine, sodium hydroxide, etc., or a dehydrating agent such as dicyclohexylcarbodiimide, concentrated sulfuric acid, etc. Compounds 6 can be prepared by methods known in the art (e.g., D. J. Hart, et. al., *J. Org. Chem.* (1983), 48, 289–294), S. -I. Murahashi, et. al., *J. Org. Chem.* (1989), 54, 3292, G. Cardillo, et. al., *J. Org. Chem.* (1986), 51, 713).

Scheme 4

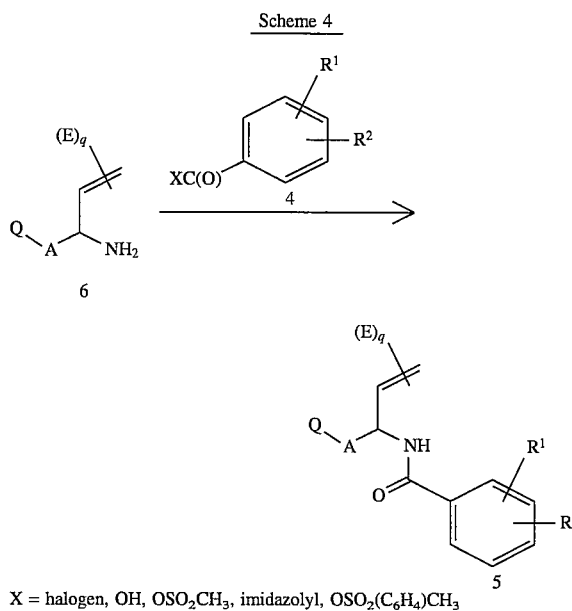

X = halogen, OH, OSO$_2$CH$_3$, imidazolyl, OSO$_2$(C$_6$H$_4$)CH$_3$

Alternatively, compounds of this invention can be prepared as in Scheme 5. The reaction is carried out with no solvent or in an inert solvent such as water, alcohol, tetrahydrofuran, benzene, chloroform, acetonitrile, N,N-dimethylformamide, dioxane, dichloromethane, etc., at a temperature of −20° C. to the boiling point of the inert solvent for several min to five days using, as desired, a base such as sodium hydride, sodium hydroxide, sodium carbonate, triethylamine, pyridine, etc. If a sulfurizing reagent such as Lawesson's reagent or phosphorus pentasulfide, etc., is used, a compound having a sulfur atom for Z is obtained.

Scheme 5

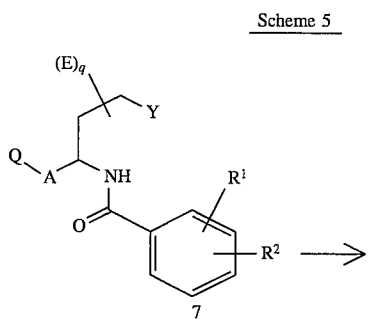

-continued
Scheme 5

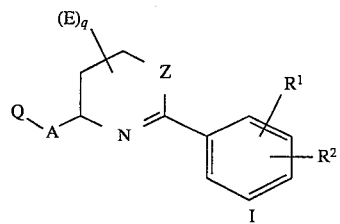

Y = halogen, OSO$_2$R, OC(O)R

The compounds 7 are prepared from compounds 2, whose preparation is described previously, by the reaction of Scheme 6. The reaction is carried out with no solvent or in an inert solvent such as benzene, tetrahydrofuran, chloroform, etc., at a temperature of −20° C. to the boiling point of the inert solvent for 30 min to 72 h using a halogenating agent such as thionyl chloride, phosphorus oxychloride, phosphorus trichloride, phosphorus pentachloride, etc., a sulfonating agent RSO$_2$L (where R=alkyl, haloalkyl, aryl, etc., and L=halogen, OSO$_2$R, etc.) or an acylating agent RC(O)L' (where R is as above, and L'=halogen, imidazole, OC(O)R, etc.) and a base such as triethylamine, pyridine, sodium hydroxide, sodium carbonate, etc.

Scheme 6

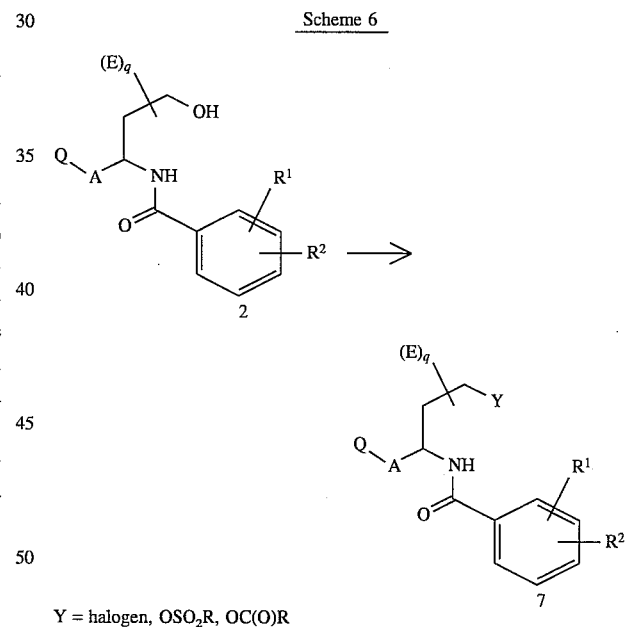

Y = halogen, OSO$_2$R, OC(O)R

Depending on the type of substituents, compounds of this invention may be prepared by carrying out reactions of the following equations or similarly known reactions, using a catalyst such as a palladium or nickel complex. Similar reactions may also be carried out on earlier intermediates, such as certain compounds of Formulae 2, 5, or 7, which can then be carried on to compounds I by the reactions shown previously.

Scheme 7

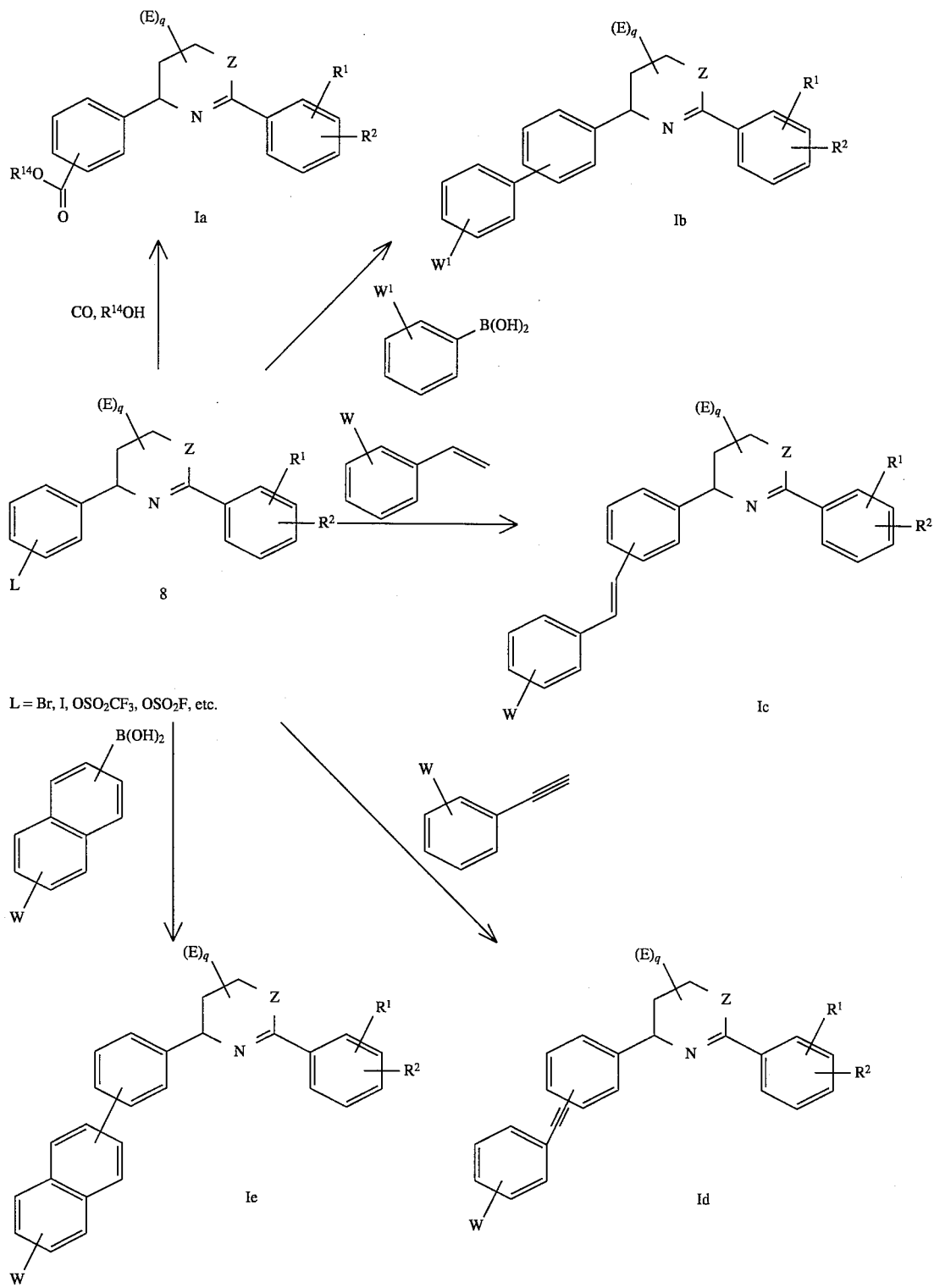

L = Br, I, OSO$_2$CF$_3$, OSO$_2$F, etc.

The desired product can be prepared by carrying out conventional post-reaction procedures after completing any of these reactions.

The structures of the compounds of this invention were identified by carrying out measurements with IR, NMR, MS, etc.

It is recognized that stone reagents and reaction conditions described above for preparing compounds of Formula I may not be compatible with certain functionalities present in the intermediates. In these instances, the incorporation of protection/deprotection sequences into the synthesis will aid in obtaining the desired products. The use and choice of the protecting group will be apparent to one skilled in chemical synthesis.

This invention is explained in detail using the application example following.

EXAMPLE 1

2-(2,6-Difluorophenyl)-4-[4-[(4-fluorophenyl)ethynyl]phenyl]-5,6-dihydro-4H-1,3-oxazine Step A: N-[1-(4-bromophenyl)-2-propenyl]-2,6-difluorobenzamide To a solution of 5.55 g of 4-bromobenzaldehyde in 15 mL of tetrahydrofuran was added 33 mL of a 1.0M solution of lithium bis(trimethylsilylamide) in tetrahydrofuran at 5°–20° C. After allowing the reaction mixture to stir at room temperature for 30 min, 30 mL of a 1.0M solution of vinylmagnesium bromide in tetrahydrofuran was added, and the mixture was heated at reflux overnight. An additional 11.5 mL of vinylmagnesium bromide solution was added, and heating was continued overnight. After allowing to cool, the reaction mixture was partitioned between ice-cold 6 NHCl solution and ether. The aqueous portion was neutralized to about pH 7 with 15% aqueous sodium hydroxide, and the product was extracted with dichloromethane. The extract was washed with water and brine, dried with magnesium sulfate, and concentrated under vacuum. The oily residue was dissolved in 15 mL of dichloromethane and cooled in an ice bath to about 5° C., 5.0 mL of triethylamine was added, and a solution of commercial 2,6-difluorobenzoyl chloride in 5 mL of dichloromethane was added. The mixture was stirred over a weekend (about 64 h) at room temperature, then it was poured into water and extracted with dichloromethane. The organic extract was washed with 1N HCl, water, and brine, dried over magnesium sulfate, and concentrated in vacuo. The residue was purified by chromatography on silica gel with 2:1 hexane/ethyl acetate elution to obtain 4.75 g of the title product. $^1$H NMR (CDCl$_3$) δ5.3–5.4-(m,2H), 5.8 (m, 1H), 6.0–6.1 (m, 1H), 6.3 (br d, 1H), 6.9–7.1 (m,3H), 7.2 (m, 1H), 7.4 (m, 1H), 7.4–7.6 (m,2H).

Step B: N-[1-(4-bromophenyl)-3-hydroxypropyl]-2,6-difluorobenzamide

A sample of compound prepared as in Step A (0.51 g) was dissolved in tetrahydrofuran at room temperature, 3.6 mL of a 0.5M solution of 9-borabicylo[3.3.1]-nonane (9-BBN) was added, and the mixture was heated at reflux. After 7 h at reflux, 3.6 mL of 9-BBN solution was added, and the mixture was heated at reflux overnight. At room temperature, 5 mL of water, 3.6 mL of 1N aqueous sodium hydroxide, and 3.6 mL of 30% aqueous hydrogen peroxide were added. After stirring for 1.5 h, this mixture was poured over ice, treated with aqueous sodium bisulfite, and extracted with ethyl acetate. The extract was washed with water and brine, dried over magnesium sulfate, and concentrated in vacuo. The residue was purified by chromatography on silica gel with hexane/ethyl acetate (2:1 to 1:3) elution to obtain the title product, 0.13 g. Unreacted starting alkene was also recovered and resubmitted to the above reaction conditions to afford an additional 0.10 g of product. 1H NMR (CDCl$_3$) δ1.9 (m, 1H), 2.2 (m, 1H), 2.6 (m, 1H), 3.7–3.9 (m,2H), 5.4 (m, 1H), 6.8 (br d, 1H), 6.9–7.0 (m,2H), 7.2–7.3 (m,2H), 7.4 (m, 1H), 7.5 (m,2H).

Step C: 4-(4-Bromophenyl)-2-(2,6-difluorophenyl)-5,6-dihydro-4H- 1,3-oxazine

In 5 mL of 1-chlorobutane, the product of Step B (0.10 g) and 1 mL of thionyl chloride were stirred and heated at reflux for 3 h. The reaction mixture was concentrated in vacuo, and 10 mL of 1-chlorobutane was twice added to the residue and the mixture reconcentrated in vacuo. The product of this reaction was dissolved in 3 mL of tetrahydrofuran and added to a suspension of 60% sodium hydride (0.016 g) in 3 mL of N,N-dimethylformamide at 0°–5° C. After 1 h, the reaction mixture was poured over ice and aqueous ammonium chloride and extracted with ethyl ether. The extract was washed with water and brine, dried over magnesium sulfate and concentrated in vacuo. The residue was purified by chromatography on silica gel with hexane/ethyl acetate (3:1) elution to afford the title product, 0.07 g. $^1$H NMR (CDCl$_3$) δ2.0 (m, 1H), 2.4 (m, 1H), 4.3 (m, 1H), 4.4 (m, 1H), 4.8 (m, 1H), 6.9 (m,2H), 7.2 (m,2H), 7.3 (m, 1H), 7.5 (m,2H), Step D: 2-(2,6-Difluorophenyl)-4-[4-[(4-fluorophenyl)ethynyl]phenyl]-5,6-dihydro-4H-1,3-oxazine In 2 mL of dichloromethane, the product of Step C (0.07 g) was combined with tetrakis(triphenylphosphine)palladium(0) (0.010 g), copper(I) iodide (0.006 g), triphenylphosphine (0.006 g), (4-fluorophenyl)acetylene (prepared by the method of A.D. Allen and C. D. Cook, Can. J. Chem. (1963), 41, 1084; 0.15 g), and triethylamine (2 mL) and the mixture heated at reflux until thin layer chromatographic analysis showed consumption of starting material. The mixture was concentrated in vacuo. The residue was purified by chromatography on silica gel to afford the title product, a compound of this invention, as a solid melting at 95°–110° C. (material prepared on larger scale, identical by $^1$H NMR spectroscopy, was recrystallized from ethyl acetate/hexane to give a solid melting at 102°–104° C.). $^1$H NMR (CDCl$_3$) δ2.0 (m, 1H), 2.4 (m, 1H), 4.3 (m, 1H), 4.5 (m, 1H), 4.8 (m, 1H), 6.9–7.1 (m,4H), 7.3–7.4 (m,3H), 7.5–7.6 (m,4H).

EXAMPLE 2

2-(2,6-Difluorophenyl)-4-[4-[(4-fluorophenyl)ethynyl]phenyl]-5,6-dihydro-4-methyl-4H-1,3-oxazine Example 2 was prepared following the procedures used for the preparation of Example 1, but with the substitution of isopropenyl magnesium bromide (prepared from magnesium metal and 2-bromopropene) for the vinyl magnesium bromide in Step A. All other steps were performed as for Example 1 to afford 0.13 g of the desired product from 11.10 g of 4-bromobenzaldehyde. The product was isolated as a 3.5:1 ratio of diastereomers (determined by integration of similar resonances in the $^1$H NMR spectrum) as a solid melting at 131°–137° C. $^1$H NMR (CDCl$_3$)δ0.8 and 1.0 (d,d3H total), 2.0 and 2.4 (m, m,1H total), 4.1 and 4.3 (m, m,2H total), 4.5 and 4.9 (m,m,1H total), 6.9 (m,2H), 7.0 (m,2H), 7.2–7.43 (m,3H), 7.5–7.6 (m,4H).

By the procedures described herein the following compounds of Tables 1 to 9 can be prepared. The compounds in Table 1, line 1 can be referred to as 1-1, 1-2, and 1-3 (as designated by line and column). All the other specific compounds covered in these Tables can be designated in an analogous fashion. The following abbreviations have been used in Tables 1–9: Me=methyl, Et=ethyl, Pr=n-propyl, iPr=isopropyl, Ph=phenyl.

TABLE 1

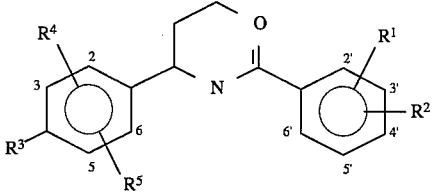

| $R^1=2'$-F, $R^2=6'$-F, $R^4=R^5=H$, $R^3=$ | | |
|---|---|---|
| | COLUMN 1 | COLUMN 2 |
| 1 | 2-chloro-2-propenyl | 2,2-dichloroethenyl |
| 2 | $CH_2SiMe_3$ | $CH_2SiMe_2Ph$ |
| 3 | $CH_2CH_2CH_2CN$ | $CH_2CH_2C(O)OMe$ |
| 4 | $O(CH_2)_3SiMe_3$ | $CH_2CH_2C(O)OCH_2CF_3$ |
| 5 | $OCH_2SiMe_3$ | $CF_2CH_2CH_2C(O)OEt$ |
| 6 | $CH_2C(O)CH_3$ | $CH_2C(O)CF_3$ |
| 7 | $OCH_2CN$ | $OCH_2C(O)CH_3$ |
| 8 | $OCH_2CH_2CN$ | $OCH_2C(O)CH_2CF_3$ |
| 9 | $O(CH_2)_6CN$ | $OCH_2C(O)OMe$ |
| 10 | $OCH_2C(O)OEt$ | $OCH_2C(O)OPr$ |
| 11 | $OCH_2C(O)O$-i-Pr | $OCH_2CH_2C(O)OMe$ |
| 12 | $C(O)OPh$ | $O(CH_2)_5C(O)OMe$ |
| 13 | $OCH_2C(O)OCH_2CF_3$ | $C(O)OMe$ |
| 14 | $C(O)OEt$ | $CH_2CH_2NO_2$ |
| 15 | $C(O)O$-i-Pr | $C(O)NH(4$-Cl$-$Ph$)$ |
| 16 | $C(O)NMe_2$ | $C(O)NHPh$ |
| 17 | $C(O)NH$-i-Pr | $C(O)N(Me)Ph$ |
| 18 | $C(O)NH(CH_2)_4CH_3$ | $C(O)CH_2CF_3$ |
| 19 | $C(O)Et$ | $C(O)OCH_2CF_3$ |
| 20 | $C(O)Ph$ | $C(O)$-4-Cl$-$Ph |
| 21 | 2-tetrahydropyranyl | $OCH=CHCN$ |
| 22 | cyclobutyloxy | $OCH=CHC(O)OEt$ |
| 23 | cyclohexyloxy | cycloheptyloxy |
| 24 | $OCH_2$-cyclopropyl | $OCH_2$-cyclopentyl |
| 25 | $OCH_2C(Cl)=CH_2$ | cyclopentyloxy |
| 26 | $OCH_2CH=C(Cl)_2$ | $OCH_2C(Br)=CH_2$ |

| $R^1=2'$-F, $R^2=6'$-F, $R^4=R^5=H$, $R^3=$ | | | |
|---|---|---|---|
| | COLUMN 1 | COLUMN 2 | COLUMN 3 |
| 27 | 2-CN$-$Ph | 2-benzothienyl | $C\equiv C(2$-$CF_3-$Ph$)$ |
| 28 | 3-CN$-$Ph | 3-benzothienyl | $C\equiv C(3$-$CF_3-$Ph$)$ |
| 29 | 4-CN$-$Ph | 5-benzothienyl | $C\equiv C(2$-$CH_3-$Ph$)$ |
| 30 | 4-$NO_2-$Ph | 5-benzodioxolyl | $C\equiv C(3$-$CH_3-$Ph$)$ |
| 31 | 4-$SF_5-$Ph | 2-benzoxazolyl | $C\equiv C(4$-$CH_3-$Ph$)$ |
| 32 | 4-$SO_2Me-$Ph | 5-benzoxazolyl | $C\equiv C(2$-$OMe-$Ph$)$ |
| 33 | 4-SEt-Ph | 6-chromanyl | $C\equiv C(3$-$OMe-$Ph$)$ |
| 34 | 4-$SCF_3-$Ph | 1-Me-3-indolinyl | $C\equiv C(4$-$OMe-$Ph$)$ |
| 35 | 4-$CO_2Me-$Ph | 6-benzodioxanyl | $C\equiv C(4$-$SMe-$Ph$)$ |
| 36 | 4-$CO_2$Et-Ph | 4-indanyl | $C\equiv C(4$-$CN-$Ph$)$ |
| 37 | 4-$C(O)CH_3-$Ph | 5-indanyl | $C\equiv C(3$-$CN-$Ph$)$ |
| 38 | 4-CHO$-$Ph | $C\equiv C-$Ph | $C\equiv C(4$-$C(O)CH_3-$Ph$)$ |
| 39 | 1-naphthyl | $C\equiv C(4$-$F-$Ph$)$ | $C\equiv C(4$-$SF_5-$Ph$)$ |
| 40 | 6-Cl-2-naphthyl | $C\equiv C(3$-$F-$Ph$)$ | $C\equiv C(3$-$Br-$Ph$)$ |
| 41 | 6-tetralinyl | $C\equiv C(2$-$F-$Ph$)$ | $C\equiv C(4$-$Br-$Ph$)$ |
| 42 | 5-tetralinyl | $C\equiv C(4$-$Cl-$Ph$)$ | $C\equiv C(2,4$-di-$F-$Ph$)$ |
| 43 | 2-quinolyl | $C\equiv C(4$-$CF_3-$Ph$)$ | $C\equiv C(3,5$-di-$F-$Ph$)$ |
| 44 | 3-quinolyl | $C(O)(4$-$F-$Ph$)$ | $C\equiv C(3,4$-di-$F-$Ph$)$ |

TABLE 1-continued

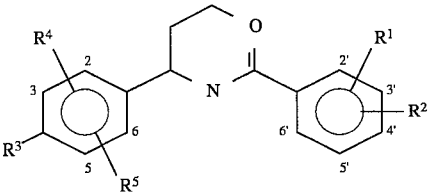

| | | | |
|---|---|---|---|
| 45 | 1-isoquinolyl | C(O)(3-F—Ph) | C≡C(3,5-di-Cl—Ph) |
| 46 | 3-isoquinolyl | C(O)(2-F—Ph) | C≡C(3,4-di-Cl—Ph) |
| 47 | 2-quinoxalinyl | CH=CH(4-F—Ph) | C≡C(3-OCF$_2$H—Ph) |
| 48 | 6-quinoxalinyl | CH=CH(3-F—Ph) | C≡C(4-OCF$_2$H—Ph) |
| 49 | 2-benzofuranyl | CH=CH(2-F—Ph) | C≡C(4-OCF$_3$—Ph) |
| 50 | 3-benzofuranyl | CH=CH(4-Cl—Ph) | C≡C(4-OCH$_2$CF$_3$—Ph) |
| 51 | 5-benzofuranyl | CH=CH—Ph | C≡C(2-CN—Ph) |
| 52 | 6-benzofuranyl | CH=CH(4-CF$_3$—Ph) | C≡C(2-F-4-Cl—Ph) |
| 53 | C≡C(2,4-di-Cl—Ph) | CH=CH(2—Cl—Ph) | C≡C(4-NO$_2$—Ph) |
| 54 | CH=CH(2-pyridyl) | CH=CH(4-pyridyl) | |

$R^1 = 2'$-F, $R^2 = 6'$-F, $R^4 = R^5 = H$, $R^3 =$

| | COLUMN 1 | COLUMN 2 | COLUMN 3 |
|---|---|---|---|
| 55 | CH=NOCH$_2$(4-F—Ph) | 4-(OCH$_2$CH=CH$_2$)—Ph | CH$_2$CH=CH(4-F—Ph) |
| 56 | C(CH$_3$)=NOCH$_3$ | 3-(OCH$_2$CH=CH$_2$)—Ph | CH$_2$CH=CH(3-F—Ph) |
| 57 | CH=NOCH$_2$CF$_3$ | 4-(OCH$_2$C≡CH)—Ph | 3-(OCH$_2$C(CH$_3$)=CH$_2$)—Ph |
| 58 | CH=NOPh | 3-(OCH$_2$C≡CH)—Ph | 4-(OCH$_2$C(Cl)=CH$_2$)—Ph |
| 59 | O—N=CHPh | 4-(OCH$_2$C(CH$_3$)=CH$_3$)—Ph | 3-(OCH$_2$C(Cl)=CH$_2$)—Ph |
| 60 | ON=C(CH$_3$)Ph | CH=CH$_2$ | C≡CSiMe$_3$ |
| 61 | ON=C(CH$_3$)(4-F—Ph) | CH=CCl$_2$ | C≡CSiMe$_2$Ph |
| 62 | C≡CCl | C≡CH | CH=CHCN |
| 63 | 4-(CH=CH$_2$)—Ph | 3-(CH=CHCl)—Ph | 4-(C≡CSiMe$_3$)—Ph |
| 64 | 3-(CH=CH$_2$)—Ph | 4-(C≡CH)—Ph | 3-(C≡CSiMe$_3$)—Ph |
| 65 | 4-(CH=CCl$_2$)—Ph | 3-(C≡CH)—Ph | 4-(CH=CHCN)—Ph |
| 66 | 3-(CH=CHCN)—Ph | 4-(CH=NOCH$_3$)—Ph | 3-(C(CH$_3$)=NOEt)—Ph |
| 67 | 4-(C≡CCl)—Ph | 3-(CH=NOCH$_3$)—Ph | 4-(C(CH$_3$)=NOCH$_3$)—Ph |
| 68 | 3-(C≡CCl)—Ph | 3-(C(CH$_3$)=NOEt)—Ph | |

$R^1 = 2'$-F, $R^2 = 6'$-Cl, $R^4 = R^5 = H$, $R^3 =$

| | COLUMN 1 | COLUMN 2 | COLUMN 3 |
|---|---|---|---|
| 69 | 2-chloro-2-propenyl | 2,2-dichloroethenyl | CF$_2$CH$_2$CH$_2$C(O)OEt |
| 70 | CH$_2$SiMe$_3$ | CH$_2$SiMe$_2$Ph | CH$_2$C(O)CF$_3$ |
| 71 | CH$_2$CH$_2$CH$_2$CN | CH$_2$CH$_2$C(O)OMe | OCH$_2$C(O)CH$_3$ |
| 72 | O(CH$_2$)$_3$SiMe$_3$ | CH$_2$CH$_2$C(O)OCH$_2$CF$_3$ | OCH$_2$C(O)CH$_2$CF$_3$ |
| 73 | OCH$_2$SiMe$_3$ | OCH$_2$CH$_2$CN | OCH$_2$C(O)OMe |
| 74 | CH$_2$C(O)CH$_3$ | O(CH$_2$)$_6$CN | OCH$_2$C(O)OPr |
| 75 | OCH$_2$CN | OCH$_2$C(O)OEt | OCH$_2$CH$_2$C(O)OMe |
| 76 | OCH$_2$C(O)O-i-Pr | O(CH$_2$)$_5$C(O)OMe | C(O)OEt |
| 77 | C(O)OPh | C(O)OMe | C(O)O-i-Pr |
| 78 | OCH$_2$C(O)OCH$_2$CF$_3$ | CH$_2$CH$_2$NO$_2$ | C(O)NMe$_2$ |
| 79 | C(O)NH-i-Pr | C(O)NH(4-Cl—Ph) | C(O)CH$_2$CF$_3$ |
| 80 | C(O)NH(CH$_2$)$_4$CH$_3$ | C(O)NHPh | C(O)OCH$_2$CF$_3$ |
| 81 | C(O)Et | C(O)N(Me)Ph | C(O)-4—Cl—Ph |
| 82 | C(O)Ph | OCH=CHCN | OCH$_2$-cyclopentyl |
| 83 | 2-tetrahydropyranyl | OCH=CHC(O)OEt | cyclopentyloxy |
| 84 | cyclobutyloxy | cycloheptyloxy | OCH$_2$C(Br)=CH$_2$ |
| 85 | cyclohexyloxy | OCH$_2$C(Cl)=CH$_2$ | OCH$_2$CH=C(Cl)$_2$ |
| 86 | OCH$_2$-cyclopropyl | | |

TABLE 1-continued

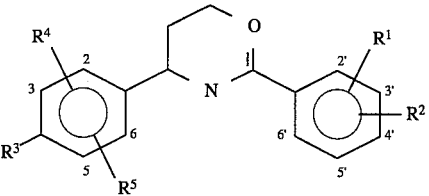

| $R^1 = 2'$-F, $R^2 = 6'$-Cl, $R^4 = R^5 = H$, $R^3 =$ | | |
|---|---|---|
| COLUMN 1 | COLUMN 2 | COLUMN 3 |
| 87 2-CN—Ph | 2-benzothienyl | C≡C(2-CF$_3$—Ph) |
| 88 3-CN—Ph | 3-benzothienyl | C≡C(3-CF$_3$—Ph) |
| 89 4-CN—Ph | 5-benzothienyl | C≡C(2-CH$_3$—Ph) |
| 90 4-NO$_2$—Ph | 5-benzodioxolyl | C≡C(3-CH$_3$—Ph) |
| 91 4-SF$_5$—Ph | 2-benzoxazolyl | C≡C(4-CH$_3$—Ph) |
| 92 4-SO$_2$Me—Ph | 5-benzoxazolyl | C≡C(2-OMe—Ph) |
| 93 4-SEt-Ph | 6-chromanyl | C≡C(3-OMe—Ph) |
| 94 4-SCF$_3$—Ph | 1-Me-3-indolinyl | C≡C(4-OMe—Ph) |
| 95 4-CO$_2$Me—Ph | 6-benzodioxanyl | C≡C(4-SMe—Ph) |
| 96 4-CO$_2$Et—Ph | 4-indanyl | C≡C(4-CN—Ph) |
| 97 4-C(O)CH$_3$—Ph | 5-indanyl | C≡C(3-CN—Ph) |
| 98 4-CHO—Ph | C≡C—Ph | C≡C(4-C(O)CH$_3$—Ph) |
| 99 1-naphthyl | C≡C(4-F—Ph) | C≡C(4-SF$_5$—Ph) |
| 100 6-Cl-2-naphthyl | C≡C(3-F—Ph) | C≡C(3-Br—Ph) |
| 101 6-tetralinyl | C≡C(2-F—Ph) | C≡C(4-Br—Ph) |
| 102 5-tetralinyl | C≡C(4-Cl—Ph) | C≡C(2,4-di-F—Ph) |
| 103 2-quinolyl | C≡C(4-CF$_3$—Ph) | C≡C(3,5-di-F—Ph) |
| 104 3-quinolyl | C(O)(4-F—Ph) | C≡C(3,4-di-F—Ph) |
| 105 1-isoquinolyl | C(O)(3-F—Ph) | C≡C(3,5-di-Cl—Ph) |
| 106 3-isoquinolyl | C(O)(2-F—Ph) | C≡C(3,4-di-Cl—Ph) |
| 107 2-quinoxalinyl | CH=CH(4-F—Ph) | C≡C(3-OCF$_2$H—Ph) |
| 108 6-quinoxalinyl | CH=CH(3-F—Ph) | C≡C(4-OCF$_2$H—Ph) |
| 109 2-benzofuranyl | CH=CH(2-F—Ph) | C≡C(4-OCF$_3$—Ph) |
| 110 3-benzofuranyl | CH=CH(4-Cl—Ph) | C≡C(4-OCH$_2$CF$_3$—Ph) |
| 111 5-benzofuranyl | CH=CH—Ph | C≡C(2-CN—Ph) |
| 112 6-benzofuranyl | CH=CH(4-CF$_3$—Ph) | C≡C(2-F-4-Cl—Ph) |
| 113 C≡C(2,4-di-Cl—Ph) | CH=CH(2-Cl—Ph) | C≡C(4-NO$_2$—Ph) |
| 114 CH=CH(2-pyridyl) | CH=CH(4-pyridyl) | |

| $R^1 = 2'$-F, $R^2 = 6'$—Cl, $R^4 = R^5 = H$, $R^3 =$ | | |
|---|---|---|
| COLUMN 1 | COLUMN 2 | COLUMN 3 |
| 115 CH=NOCH$_2$(4-F—Ph) | CH$_2$CH=CH(4-F—Ph) | 4-(OCH$_2$CH=CH$_2$)—Ph |
| 116 C(CH$_3$)=NOCH$_3$ | CH$_2$CH=CH(3-F—Ph) | 3-(OCH$_2$CH=CH$_2$)—Ph |
| 117 CH=NOCH$_2$CF$_3$ | 3-(OCH$_2$C≡CH)—Ph | 4-(OCH$_2$C≡CH)—Ph |
| 118 CH=NOPh | 4-(OCH$_2$C(CH$_3$)=CH$_2$)—Ph | CH=CH$_2$ |
| 119 O—N=CHPh | 3-(OCH$_2$C(CH$_3$)=CH$_2$)—Ph | CH=CCl$_2$ |
| 120 ON=C(CH$_3$)Ph | 4-(OCH$_2$C(Cl)=CH$_2$)—Ph | C≡CSiMe$_2$Ph |
| 121 ON=C(CH$_3$)(4-F—Ph) | 3-(OCH$_2$C(Cl)=CH$_2$)—Ph | CH=CHCN |

TABLE 1-continued

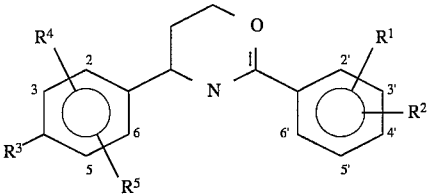

| | | | |
|---|---|---|---|
| 122 | C≡CH | C≡CCl | 4-(C≡CH)—Ph |
| 123 | C≡CSiMe₃ | 4-(CH=CH₂)—Ph | 3-(C≡CH)—Ph |
| 124 | 4-(CH=CCl₂)—Ph | 3-(CH=CH₂)—Ph | 4-(C≡CSiMe₃)—Ph |
| 125 | 3-(CH=CHCl)—Ph | 4-(C≡CCl)—Ph | 3-(CH=NOCH₃)—Ph |
| 126 | 3-(C≡CSiMe₃)—Ph | 3-(C≡CCl)—Ph | 4-(C(CH₃)=NOCH₃)—Ph |
| 127 | 4-(CH=CHCN)—Ph | 4-(CH=NOCH₃)—Ph | 3-(C(CH₃)=NOEt)—Ph |
| 128 | 3-(CH=CHCN)—Ph | | |

$R^1 = H, R^4 = H, R^5 = H$

| | COLUMN 1 | | COLUMN 2 | |
|---|---|---|---|---|
| | $R^2 =$ | $R^3 =$ | $R^2 =$ | $R^3 =$ |
| 129 | 2'-F | C≡C(4-F—Ph) | 2'-Cl | C≡C(4-F—Ph) |
| 130 | 2'-F | C≡C(4-Cl—Ph) | 2'-Cl | C≡C(4-Cl—Ph) |
| 131 | 2'-F | C≡C(2,4-di-Cl—Ph) | 2'-Cl | C≡C(2,4-di-Cl—Ph) |
| 132 | 2'-F | C≡CPh | 2'-Cl | C≡CPh |
| 133 | 2'-F | 4-CN—Ph | 2'-Cl | 4-CN—Ph |
| 134 | 2'-F | 4-SCF₃—Ph | 2'-Cl | 4-SCF₃—Ph |
| 135 | 2'-F | CH=CH(4-F—Ph) | 2'-Cl | CH=CH(4-F—Ph) |
| 136 | 2'-F | CH=CH(4-Cl—Ph) | 2'-Cl | CH=CH(4-Cl—Ph) |
| 137 | 2'-F | CH=CH(4-CF₃—Ph) | 2'-Cl | CH=CH(4-CF₃—Ph) |

$R^1 = 2'-F, R^2 = 6'-F, R^4 = 3-Cl$

| | COLUMN 1 | | COLUMN 2 | |
|---|---|---|---|---|
| | $R^5 =$ | $R^3 =$ | $R^5 =$ | $R^3 =$ |
| 138 | H | C≡C(4-F—Ph) | 5-Cl | C≡C(4-F—Ph) |
| 139 | H | C≡C(4-Cl—Ph) | 5-Cl | C≡C(4-Cl—Ph) |
| 140 | H | C≡C(2,4-di-Cl—Ph) | 5-Cl | C≡C(2,4-di-Cl—Ph) |
| 141 | H | 4-CN—Ph | 5-Cl | 4-CN—Ph |
| 142 | H | 4-SCF₃—Ph | 5-Cl | 4-SCF₃—Ph |
| 143 | H | C≡C(2,4-di-F—Ph) | 5-Cl | C≡C(2,4-di-F—Ph) |
| 144 | H | C≡C(2-F-4-Cl—Ph) | 5-Cl | C≡C(2-F-4-Cl—Ph) |
| 145 | H | 4-SMe—Ph | 5-Cl | 4-SMe—Ph |
| 146 | H | 2-naphthyl | 5-Cl | 2-naphthyl |

TABLE 2

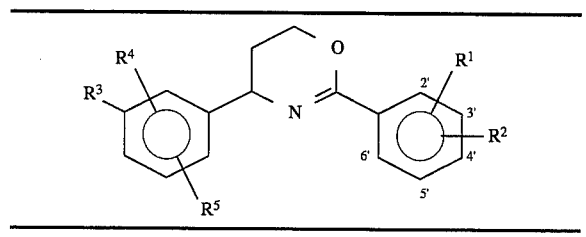

$R^1 = 2'\text{-F}, R^2 = 6'\text{-F}, R^4 = R^5 = H, R^3 =$

| | COLUMN 1 | COLUMN 2 |
|---|---|---|
| 147 | $CH_2CH_2CH_2CN$ | $C\equiv C(4\text{-F}-Ph)$ |
| 148 | $CH=CCl_2$ | $C\equiv C(4\text{-Cl}-Ph)$ |
| 149 | $CH_2C(O)CH_3$ | $C\equiv C(2,4\text{-di-Cl}-Ph)$ |
| 150 | $OCH_2C(O)CH_2CF_3$ | 2-naphthyl |
| 151 | $CH_2SiMe_3$ | $4\text{-}(CH=NOCH_3)-Ph$ |
| 152 | $C(O)OEt$ | $4\text{-}(C\equiv CH)-Ph$ |
| 153 | $C(O)\text{-}4\text{-Cl}-Ph$ | $4\text{-}(C\equiv CCl)-Ph$ |
| 154 | $OCH_2C(Cl)=CH_2$ | $4\text{-}(CH=CHCN)-Ph$ |
| 155 | $4\text{-CN}-Ph$ | $C\equiv C(3,4\text{-di-Cl}-Ph)$ |
| 156 | $4\text{-SCF}_3-Ph$ | $C\equiv C(3,4\text{-di-F}-Ph)$ |
| 157 | $CH=CH(4\text{-F}-Ph)$ | $C\equiv C(4\text{-CN}-Ph)$ |
| 158 | $CH=CH(3\text{-Cl}-Ph)$ | $C(O)NH(2\text{-F}-Ph)$ |
| 159 | $CH=CH(4\text{-CF}_3-Ph)$ | $C\equiv CH$ |
| 160 | $C\equiv CPh$ | $C\equiv CSiMe_3$ |

$R^1 = 2'\text{-F}, R^2 = 6'\text{-Cl}, R^4 = R^5 = H, R^3 =$

| | COLUMN 1 | COLUMN 2 |
|---|---|---|
| 161 | $CH_2CH_2CH_2CN$ | $C\equiv C(4\text{-F}-Ph)$ |
| 162 | $CH=CCl_2$ | $C\equiv C(4\text{-Cl}-Ph)$ |
| 163 | $CH_2C(O)CH_3$ | $C\equiv C(2,4\text{-di-Cl}-Ph)$ |
| 164 | $OCH_2C(O)CH_2CF_3$ | 2-naphthyl |
| 165 | $CH_2SiMe_3$ | $4\text{-}(CH=NOCH_3)-Ph$ |
| 166 | $C(O)OEt$ | $4\text{-}(C\equiv CH)-Ph$ |
| 167 | $C(O)\text{-}4\text{-Cl}-Ph$ | $4\text{-}(C\equiv CCl)-Ph$ |
| 168 | $OCH_2C(Cl)=CH_2$ | $4\text{-}(CH=CHCN)-Ph$ |
| 169 | $4\text{-CN}-Ph$ | $C\equiv C(3,4\text{-di-Cl}-Ph)$ |
| 170 | $4\text{-SCF}_3-Ph$ | $C\equiv C(3,4\text{-di-F}-Ph)$ |
| 171 | $CH=CH(4\text{-F}-Ph)$ | $C\equiv C(4\text{-CN}-Ph)$ |
| 172 | $CH=CH(3\text{-Cl}-Ph)$ | $C(O)NH(2\text{-F}-Ph)$ |
| 173 | $CH=CH(4\text{-CF}_3-Ph)$ | $C\equiv CH$ |
| 174 | $C\equiv CPh$ | $C\equiv CSiMe_3$ |

TABLE 3

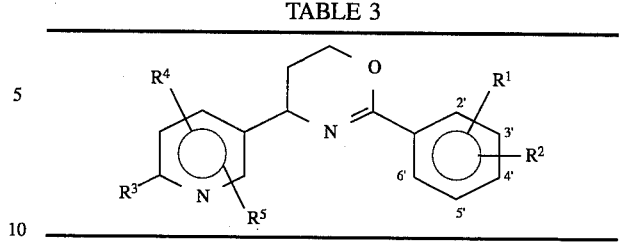

$R^1 = 2'\text{-F}, R^2 = 6'\text{-F}, R^4 = R^5 = H, R^3 =$

| | COLUMN 1 | COLUMN 2 |
|---|---|---|
| 175 | $CH_2CH_2CH_2CN$ | $C\equiv C(4\text{-F}-Ph)$ |
| 176 | $CH=CCl_2$ | $C\equiv C(4\text{-Cl}-Ph)$ |
| 177 | $CH_2C(O)CH_3$ | $C\equiv C(2,4\text{-di-Cl}-Ph)$ |
| 178 | $OCH_2C(O)CH_2CF_3$ | 2-naphthyl |
| 179 | $CH_2SiMe_3$ | $4\text{-}(CH=NOCH_3)-Ph$ |
| 180 | $C(O)OEt$ | $4\text{-}(C\equiv CH)-Ph$ |
| 181 | $C(O)\text{-}4\text{-Cl}-Ph$ | $4\text{-}(C\equiv CCl)-Ph$ |
| 182 | $OCH_2C(Cl)=CH_2$ | $4\text{-}(CH=CHCN)-Ph$ |
| 183 | $4\text{-CN}-Ph$ | $C\equiv C(3,4\text{-di-Cl}-Ph)$ |
| 184 | $4\text{-SCF}_3-Ph$ | $C\equiv C(3,4\text{-di-F}-Ph)$ |
| 185 | $CH=CH(4\text{-F}-Ph)$ | $C\equiv C(4\text{-CN}-Ph)$ |
| 186 | $CH=CH(3\text{-Cl}-Ph)$ | $C(O)NH(2\text{-F}-Ph)$ |
| 187 | $CH=CH(4\text{-CF}_3-Ph)$ | $C\equiv CH$ |
| 188 | $C\equiv CPh$ | $C\equiv CSiMe_3$ |

$R^1 = 2'\text{-F}, R^2 = 6'\text{-Cl}, R^4 = R^5 = H, R^3 =$

| | COLUMN 1 | COLUMN 2 |
|---|---|---|
| 189 | $CH_2CH_2CH_2CN$ | $C\equiv C(4\text{-F}-Ph)$ |
| 190 | $CH=CCl_2$ | $C\equiv C(4\text{-Cl}-Ph)$ |
| 191 | $CH_2C(O)CH_3$ | $C\equiv C(2,4\text{-di-Cl}-Ph)$ |
| 192 | $OCH_2C(O)CH_2CF_3$ | 2-naphthyl |
| 193 | $CH_2SiMe_3$ | $4\text{-}(CH=NOCH_3)-Ph$ |
| 194 | $C(O)OEt$ | $4\text{-}(C\equiv CH)-Ph$ |
| 195 | $C(O)\text{-}4\text{-Cl}-Ph$ | $4\text{-}(C\equiv CCl)-Ph$ |
| 196 | $OCH_2C(Cl)=CH_2$ | $4\text{-}(CH=CHCN)-Ph$ |
| 197 | $4\text{-CN}-Ph$ | $C\equiv C(3,4\text{-di-Cl}-Ph)$ |
| 198 | $4\text{-SCF}_3-Ph$ | $C\equiv C(3,4\text{-di-F}-Ph)$ |
| 199 | $CH=CH(4\text{-F}-Ph)$ | $C\equiv C(4\text{-CN}-Ph)$ |
| 200 | $CH=CH(3\text{-Cl}-Ph)$ | $C(O)NH(2\text{-F}-Ph)$ |
| 201 | $CH=CH(4\text{-CF}_3-Ph)$ | $C\equiv CH$ |
| 202 | $C\equiv CPh$ | $C\equiv CSiMe_3$ |

TABLE 4

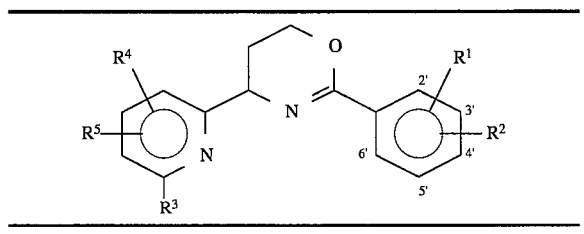

$R^1 = 2'$-F, $R^2 = 6'$-F, $R^4 = R^5 = $H, $R^3 = $

| # | COLUMN 1 | COLUMN 2 |
|---|---|---|
| 203 | CH$_2$CH$_2$CH$_2$CN | C≡C(4-F—Ph) |
| 204 | CH=CCl$_2$ | C≡C(4-Cl—Ph) |
| 205 | CH$_2$C(O)CH$_3$ | C≡C(2,4-di-Cl—Ph) |
| 206 | OCH$_2$C(O)CH$_2$CF$_3$ | 2-naphthyl |
| 207 | CH$_2$SiMe$_3$ | 4-(CH=NOCH$_3$)—Ph |
| 208 | C(O)OEt | 4-(C≡CH)—Ph |
| 209 | C(O)-4-Cl—Ph | 4-(C≡CCl)—Ph |
| 210 | OCH$_2$C(Cl)=CH$_2$ | 4-(CH=CHCN)—Ph |
| 211 | 4-CN—Ph | C≡C(3,4-di-Cl—Ph) |
| 212 | 4-SCF$_3$—Ph | C≡C(3,4-di-F—Ph) |
| 213 | CH=CH(4-F—Ph) | C≡C(4-CN—Ph) |
| 214 | CH=CH(3-Cl—Ph) | C(O)NH(2-F—Ph) |
| 215 | CH=CH(4-CF$_3$—Ph) | C≡CH |
| 216 | C≡CPh | C≡CSiMe$_3$ |

$R^1 = 2'$-F, $R^2 = 6'$-Cl, $R^4 = R^5 = $H, $R^3 = $

| # | COLUMN 1 | COLUMN 2 |
|---|---|---|
| 217 | CH$_2$CH$_2$CH$_2$CN | C≡C(4-F—Ph) |
| 218 | CH=CCl$_2$ | C≡C(4-Cl—Ph) |
| 219 | CH$_2$C(O)CH$_3$ | C≡C(2,4-di-Cl—Ph) |
| 220 | OCH$_2$C(O)CH$_2$CF$_3$ | 2-naphthyl |
| 221 | CH$_2$SiMe$_3$ | 4-(CH=NOCH$_3$)—Ph |
| 222 | C(O)OEt | 4-(C≡CH)—Ph |
| 223 | C(O)-4-Cl—Ph | 4-(C≡CCl)—Ph |
| 224 | OCH$_2$C(Cl)=CH$_2$ | 4-(CH=CHCN)—Ph |
| 225 | 4-CN—Ph | C≡C(3,4-di-Cl—Ph) |
| 226 | 4-SCF$_3$—Ph | C≡C(3,4-di-F—Ph) |
| 227 | CH=CH(4-F—Ph) | C≡C(4-CN—Ph) |
| 228 | CH=CH(3-Cl—Ph) | C(O)NH(2-F—Ph) |
| 229 | CH=CH(4-CF$_3$—Ph) | C≡CH |
| 230 | C≡CPh | C≡CSiMe$_3$ |

TABLE 5

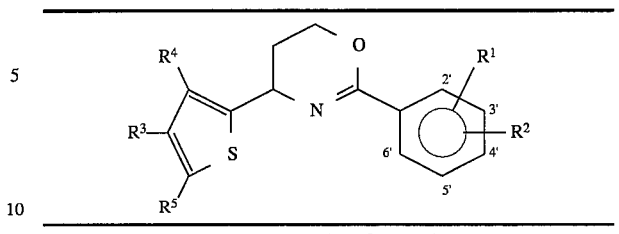

$R^1 = 2'$-F, $R^2 = 6'$-F, $R^4 = R^5 = $H, $R^3 = $

| # | COLUMN 1 | COLUMN 2 |
|---|---|---|
| 231 | CH$_2$CH$_2$CH$_2$CN | C≡C(4-F—Ph) |
| 232 | CH=CCl$_2$ | C≡C(4-Cl—Ph) |
| 233 | CH$_2$C(O)CH$_3$ | C≡C(2,4-di-Cl—Ph) |
| 234 | OCH$_2$C(O)CH$_2$CF$_3$ | 2-naphthyl |
| 235 | CH$_2$SiMe$_3$ | 4-(CH=NOCH$_3$)—Ph |
| 236 | C(O)OEt | 4-(C≡CH)—Ph |
| 237 | C(O)-4-Cl—Ph | 4-(C≡CCl)—Ph |
| 238 | OCH$_2$C(Cl)=CH$_2$ | 4-(CH=CHCN)—Ph |
| 239 | 4-CN—Ph | C≡C(3,4-di-Cl—Ph) |
| 240 | 4-SCF$_3$—Ph | C≡C(3,4-di-F—Ph) |
| 241 | CH=CH(4-F—Ph) | C≡C(4-CN—Ph) |
| 242 | CH=CH(3-Cl—Ph) | C(O)NH(2-F—Ph) |
| 243 | CH=CH(4-CF$_3$—Ph) | C≡CH |
| 244 | C≡CPh | C≡CSiMe$_3$ |

$R^1 = 2'$-F, $R^2 = 6'$-Cl, $R^4 = R^5$H, $R^3 = $

| # | COLUMN 1 | COLUMN 2 |
|---|---|---|
| 245 | CH$_2$CH$_2$CH$_2$CN | C≡C(4-F—Ph) |
| 246 | CH=CCl$_2$ | C≡C(4-Cl—Ph) |
| 247 | CH$_2$C(O)CH$_3$ | C≡C(2,4-di-Cl—Ph) |
| 248 | OCH$_2$C(O)CH$_2$CF$_3$ | 2-naphthyl |
| 249 | CH$_2$SiMe$_3$ | 4-(CH=NOCH$_3$)—Ph |
| 250 | C(O)OEt | 4-(C≡CH)—Ph |
| 251 | C(O)-4-Cl—Ph | 4-(C≡CCl)—Ph |
| 252 | OCH$_2$C(Cl)=CH$_2$ | 4-(CH=CHCN)—Ph |
| 253 | 4-CN—Ph | C≡C(3,4-di-Cl—Ph) |
| 254 | 4-SCF$_3$—Ph | C≡C(3,4-di-F—Ph) |
| 255 | CH=CH(4-F—Ph) | C≡C(4-CN—Ph) |
| 256 | CH=CH(3-Cl—Ph) | C(O)NH(2-F—Ph) |
| 257 | CH=CH(4-CF$_3$—Ph) | C≡CH |
| 258 | C≡CPh | C≡CSiMe$_3$ |

TABLE 6

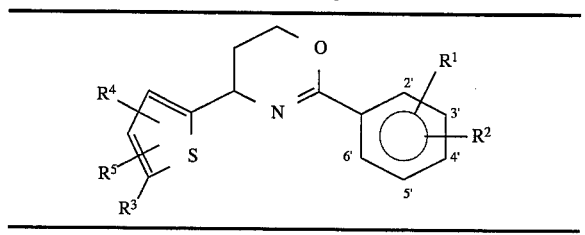

R¹=2'-F, R²=6'-F, R⁴=R⁵=H, R³=

| | COLUMN 1 | COLUMN 2 |
|---|---|---|
| 259 | $CH_2CH_2CH_2CN$ | $C{\equiv}C(4\text{-}F\text{-}Ph)$ |
| 260 | $CH{=}CCl_2$ | $C{\equiv}C(4\text{-}Cl\text{-}Ph)$ |
| 261 | $CH_2C(O)CH_3$ | $C{\equiv}C(2,4\text{-di-}Cl\text{-}Ph)$ |
| 262 | $OCH_2C(O)CH_2CF_3$ | 2-naphthyl |
| 263 | $CH_2SiMe_3$ | $4\text{-}(CH{=}NOCH_3)\text{-}Ph$ |
| 264 | $C(O)OEt$ | $4\text{-}(C{\equiv}CH)\text{-}Ph$ |
| 265 | $C(O)\text{-}4\text{-}Cl\text{-}Ph$ | $4\text{-}(C{\equiv}CCl)\text{-}Ph$ |
| 266 | $OCH_2C(Cl){=}CH_2$ | $4\text{-}(CH{=}CHCN)\text{-}Ph$ |
| 267 | $4\text{-}CN\text{-}Ph$ | $C{\equiv}C(3,4\text{-di-}Cl\text{-}Ph)$ |
| 268 | $4\text{-}SCF_3\text{-}Ph$ | $C{\equiv}C(3,4\text{-di-}F\text{-}Ph)$ |
| 269 | $CH{=}CH(4\text{-}F\text{-}Ph)$ | $C{\equiv}C(4\text{-}CN\text{-}Ph)$ |
| 270 | $CH{=}CH(3\text{-}Cl\text{-}Ph)$ | $C(O)NH(2\text{-}F\text{-}Ph)$ |
| 271 | $CH{=}CH(4\text{-}CF_3\text{-}Ph)$ | $C{\equiv}CH$ |
| 272 | $C{\equiv}CPh$ | $C{\equiv}CSiMe_3$ |

R¹=2'-F, R²=6'-Cl, R⁴=R⁵=H, R³=

| | COLUMN 1 | COLUMN 2 |
|---|---|---|
| 273 | $CH_2CH_2CH_2CN$ | $C{\equiv}C(4\text{-}F\text{-}Ph)$ |
| 274 | $CH{=}CCl_2$ | $C{\equiv}C(4\text{-}Cl\text{-}Ph)$ |
| 275 | $CH_2C(O)CH_3$ | $C{\equiv}C(2,4\text{-di-}Cl\text{-}Ph)$ |
| 276 | $OCH_2C(O)CH_2CF_3$ | 2-naphthyl |
| 277 | $CH_2SiMe_3$ | $4\text{-}(CH{=}NOCH_3)\text{-}Ph$ |
| 278 | $C(O)OEt$ | $4\text{-}(C{\equiv}CH)\text{-}Ph$ |
| 279 | $C(O)\text{-}4\text{-}Cl\text{-}Ph$ | $4\text{-}(C{\equiv}CCl)\text{-}Ph$ |
| 280 | $OCH_2C(Cl){=}CH_2$ | $4\text{-}(CH{=}CHCN)\text{-}Ph$ |
| 281 | $4\text{-}CN\text{-}Ph$ | $C{\equiv}C(3,4\text{-di-}Cl\text{-}Ph)$ |
| 282 | $4\text{-}SCF_3\text{-}Ph$ | $C{\equiv}C(3,4\text{-di-}F\text{-}Ph)$ |
| 283 | $CH{=}CH(4\text{-}F\text{-}Ph)$ | $C{\equiv}C(4\text{-}CN\text{-}Ph)$ |
| 284 | $CH{=}CH(3\text{-}Cl\text{-}Ph)$ | $C(O)NH(2\text{-}F\text{-}Ph)$ |
| 285 | $CH{=}CH(4\text{-}CF_3\text{-}Ph)$ | $C{\equiv}CH$ |
| 286 | $C{\equiv}CPh$ | $C{\equiv}CSiMe_3$ |

TABLE 7

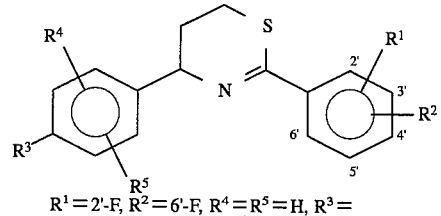

R¹=2'-F, R²=6'-F, R⁴=R⁵=H, R³=

| | COLUMN 1 | COLUMN 2 |
|---|---|---|
| 287 | $CH_2CH_2CH_2CN$ | $C{\equiv}C(4\text{-}F\text{-}Ph)$ |
| 288 | $CH{=}CCl_2$ | $C{\equiv}C(4\text{-}Cl\text{-}Ph)$ |
| 289 | $CH_2C(O)CH_3$ | $C{\equiv}C(2,4\text{-di-}Cl\text{-}Ph)$ |
| 290 | $OCH_2C(O)CH_2CF_3$ | 2-naphthyl |
| 291 | $CH_2SiMe_3$ | $4\text{-}(CH{=}NOCH_3)\text{-}Ph$ |
| 292 | $C(O)OEt$ | $4\text{-}(C{\equiv}CH)\text{-}Ph$ |
| 293 | $C(O)\text{-}4\text{-}Cl\text{-}Ph$ | $4\text{-}(C{\equiv}CCl)\text{-}Ph$ |
| 294 | $OCH_2C(Cl){=}CH_2$ | $4\text{-}(CH{=}CHCN)\text{-}Ph$ |
| 295 | $4\text{-}CN\text{-}Ph$ | $C{\equiv}C(3,4\text{-di-}Cl\text{-}Ph)$ |
| 296 | $4\text{-}SCF_3\text{-}Ph$ | $C{\equiv}C(3,4\text{-di-}F\text{-}Ph)$ |
| 297 | $CH{=}CH(4\text{-}F\text{-}Ph)$ | $C{\equiv}C(4\text{-}CN\text{-}Ph)$ |
| 298 | $CH{=}CH(3\text{-}Cl\text{-}Ph)$ | $C(O)NH(2\text{-}F\text{-}Ph)$ |
| 299 | $CH{=}CH(4\text{-}CF_3\text{-}Ph)$ | $C{\equiv}CH$ |
| 300 | $C{\equiv}CPh$ | $C{\equiv}CSiMe_3$ |

TABLE 8

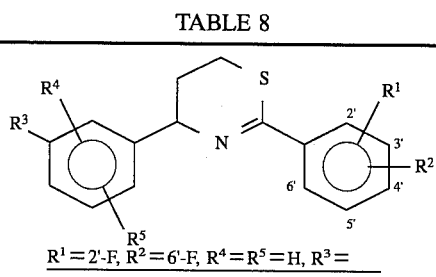

R¹=2'-F, R²=6'-F, R⁴=R⁵=H, R³=

| | COLUMN 1 | COLUMN 2 |
|---|---|---|
| 301 | $CH_2CH_2CH_2CN$ | $C{\equiv}C(4\text{-}F\text{-}Ph)$ |
| 302 | $CH{=}CCl_2$ | $C{\equiv}C(4\text{-}Cl\text{-}Ph)$ |
| 303 | $CH_2C(O)CH_3$ | $C{\equiv}C(2,4\text{-di-}Cl\text{-}Ph)$ |
| 304 | $OCH_2C(O)CH_2CF_3$ | 2-naphthyl |
| 305 | $CH_2SiMe_3$ | $4\text{-}(CH{=}NOCH_3)\text{-}Ph$ |
| 306 | $C(O)OEt$ | $4\text{-}(C{\equiv}CH)\text{-}Ph$ |
| 307 | $C(O)\text{-}4\text{-}Cl\text{-}Ph$ | $4\text{-}(C{\equiv}CCl)\text{-}Ph$ |
| 308 | $OCH_2C(Cl){=}CH_2$ | $4\text{-}(CH{=}CHCN)\text{-}Ph$ |
| 309 | $4\text{-}CN\text{-}Ph$ | $C{\equiv}C(3,4\text{-di-}Cl\text{-}Ph)$ |
| 310 | $4\text{-}SCF_3\text{-}Ph$ | $C{\equiv}C(3,4\text{-di-}F\text{-}Ph)$ |
| 311 | $CH{=}CH(4\text{-}F\text{-}Ph)$ | $C{\equiv}C(4\text{-}CN\text{-}Ph)$ |
| 312 | $CH{=}CH(3\text{-}Cl\text{-}Ph)$ | $C(O)NH(2\text{-}F\text{-}Ph)$ |
| 313 | $CH{=}CH(4\text{-}CF_3\text{-}Ph)$ | $C{\equiv}CH$ |
| 314 | $C{\equiv}CPh$ | $C{\equiv}CSiMe_3$ |

TABLE 9

[Structure: Benzene ring with R³ (para), R⁴ (meta-ish), R⁵ substituents, bearing a CH(CH₂CH₂-O-) group connected via N=C to another benzene ring with R¹ (2'), R² (4'), positions 3', 5', 6' labeled]

$R^1 = F$, $R^4 = R^5 = H$

| | $R^2$ | $R^3$ |
|---|---|---|
| 315 | 4-F | CH=CH(4-F—Ph) |
| 316 | 4-Cl | CH=CH(3-F—Ph) |
| 317 | 4-Me | CH=CH(4-Cl—Ph) |
| 318 | 4-CF₃ | CH=CH(3-Cl—Ph) |
| 319 | 2-OMe | CH=CH(3-OCHF₂—Ph) |
| 320 | 2-OCF₃ | C≡C(4-F—Ph) |
| 321 | 2-OCHCF₂ | C≡C(4-Cl—Ph) |
| 322 | 4-SMe | C≡C(3-OCHF₂—Ph) |
| 323 | 2-CN | 4-CN—Ph |
| 324 | 4-NO₂ | 3-CH=NOMe—Ph |

Formulation/Utility

Compounds of this invention will generally be used in formulation with an agriculturally suitable carrier comprising a liquid or solid diluent and/or a surfactant wherein the formulation is consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–74 | 1–15 |
| Suspensions, Emulsions, Solutions (including Emulsifiable Concentrates) | 5–50 | 40–95 | 0–15 |
| Dusts | 1–25 | 70–99 | 0–5 |

| | Weight Percent | | |
|---|---|---|---|
| | Active Ingredient | Diluent | Surfactant |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltarates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cottonseed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control*

*as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional way. Example numbers refer to compounds in Index Table A.

Example A

Wettable Powder

| | |
|---|---|
| Example 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Example 1 | 10.0% |
| attapulgite granules (low volatile matter, 0.71/0.30 mm; U.S.S. No. 25–50 sieves) | 90.0%. |

Example C

Extruded Pellet

| | |
|---|---|
| Example 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Example 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae, Tetranychus cinnabarinus, Tetranychus mcdanieli, Tetranychus pacificus, Tetranychus turkestani, Byrobia rubrioculus, Panonychus ulmi, Panonychus citri, Eotetranychus carpini borealis, Eotetranychus, hicoriae, Eotetranychus sexmaculatus, Eotetranychus yumensis, Eotetranychus banksi* and *Oligonychus pratensis;* Tenuipalpidae including *Brevipalpus lewisi, Brevipalpus phoenicis, Brevipalpus californicus* and *Brevipalpus obovatus;* Eriophyidae including *Phyllocoptruta oleivora, Eriophyes sheldoni, Aculus cornutus, Epitrimerus pyri* and *Eriophyes mangiferae.* See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as avermectin B, monocrotophos, carbofuran, tetrachlorvinphos, malathion, parathion-methyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, methamidophos, phosmet, phosphamidon, phosalone, pirimicarb, phorate, terbufos, trichlorfon, methoxychlor, diafenthiuron, bifenthrin, biphenate, cyfluthrin, tefluthrin, fenpropathrin, fluvalinate, flucythrinate, tebufenozide, tralomethrin, imidacloprid, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-A1, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as oxytetracyline, streptomycin and tribasic copper sulfate; acaricides such as binapacryl, fenpropathrin, pyridaben, fenazaquin, fenpyroximate, oxythioquinox, chlorobenzilate, dicofol, dienochlor, cyhexatin, hexythiazox, amitraz, propargite, tebufenpyrad and fenbutatin oxide; and biological agents such as entomopathogenic bacteria, virus and fungi.

In certain instances, combinations with other arthropodicides having a similar spectrum of control but a different mode of action will be particularly advantageous for resistance management.

Preferred commercial compounds that can be mixed with compounds of this invention for better control of pests (use rate or spectrum) or resistance management are avermectin B, methomyl, fipronil, imidachloprid, propargite, fenpropathrin, tebufenpyrad, pyridaben and lebufenozide. Specifically preferred are mixtures of a compound of Formula I with tebufenozide.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of Formula I, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. The pest control protection afforded by the compounds is not limited, however, to these species. See Index Table A for compound descriptions.

INDEX TABLE A

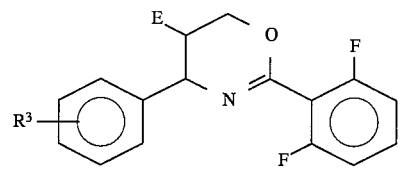

| Example No. | $R^3$ | E | Physical Properties |
|---|---|---|---|
| 1 | 4-(4-F—Ph—C≡C—) | H | mp 102–104°C. |
| 2 | 4-(4-F—Ph—C≡C—) | Me | mp 131–137°C. |

TEST A

Larval two-Spotted Spider Mites (*Tetranychus urticae*)

Solutions of the test compounds were prepared by dissolving in a minimum of acetone and then adding water containing a wetting agent until the concentration of the compound was 50 ppm. Two-week old red kidney bean plants infested with two-spotted spider mites eggs were sprayed to run-off (equivalent to 28 g/ha) with the test solution using a turntable sprayer. Plants were held in a chamber at 25° C. and 50% relative humidity. Of the compounds tested, the following gave mortality levels of 80% or higher seven days after spraying: 1.

TEST B

Fall Armyworm Whole Plant Test

Solutions of the test compounds were prepared by dissolving in a minimum of acetone and adding water containing a wetting agent until the concentration of the compounds was 10 ppm. Test compounds were then sprayed to run-off (equivalent to 5.5 g/ha) onto soybean plants utilizing a rotating platform and an atomizing sprayer. Treated plants were dried, and fall armyworm (*Spodoptera frugiperda*) larvae were exposed to excised, treated leaves. Test units were held at 27° C. and 50% relative humidity, and evaluated for larval mortality 120 h post-infestation. Of the compounds tested, the following gave mortality levels of 80% or higher: 1.

We claim:

1. A compound of Formula I

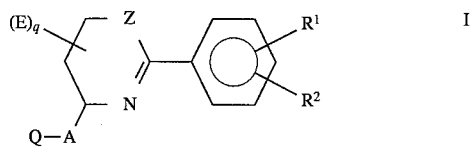

or an agriculturally-suitable salt thereof;
wherein:

A is selected from the group direct bond, $C_1$–$C_3$ alkylene and $C_2$–$C_4$ alkenylene;

Q is selected from the group phenyl, and pyridyl, each ring substituted with $R^3$, $R^4$ and $R^5$;

E is selected from the group $C_1$–$C_4$ alkyl and $C_1$–$C_4$ haloalkyl;

Z is selected from the group O and S;

$R^1$ and $R^2$ are independently selected from the group H, and halogen;

$R^3$ is selected from the group $C_2$–$C_{10}$ alkenyl optionally substituted with at least one member independently selected from $R^9$; $C_2$–$C_{10}$ alkynyl optionally substituted with at least one member independently selected from $R^9$; and phenyl substituted with at least one member independently selected from $W^1$;

$R^4$ and $R^5$ are independently selected from the group H, halogen, CN, $NO_2$, $C_1$–$C_{16}$ alkyl, $C_1$–$C_{16}$ alkoxy, $C_1$–$C_{16}$ haloalkyl, $C_1$–$C_{16}$ haloalkoxy, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, and phenyl optionally substituted with at least one member independently selected from W;

$R^6$ and $R^7$ are independently selected from the group $C_1$–$C_6$ alkyl;

$R^8$ is selected from the group $C_1$–$C_6$ alkyl and phenyl optionally substituted with W;

$R^9$ is selected from the group halogen, CN and $Si(R^6)(R^7)(R^8)$; or $R^9$ is selected from the group phenyl and pyridyl, each optionally substituted with at least one member independently selected from W;

$R^{10}$ and $R^{11}$ are independently selected from the group H, $C_1$–$C_6$ alkyl, $C_1$–$C_6$ haloalkyl, phenyl optionally substituted with at least one member independently selected from W, and benzyl optionally substituted with at least one member independently selected from W;

$R^{13}$ is selected from the group $C_1$–$C_3$ alkyl and $C_1$–$C_3$ haloalkyl;

W is selected from the group halogen, CN, CHO, $NO_2$, $SF_5$, $C_1$–$C_3$ alkyl, $C_1$–$C_3$ haloalkyl, $C_1$–$C_3$ alkylthio, $C_1$–$C_3$ alkoxy, $C_1$–$C_3$ haloalkoxy, $C_2$–$C_4$ alkylcarbonyl and $C_2$–$C_4$ alkoxycarbonyl;

$W^1$ is selected from the group CN, CHO, $NO_2$, $SF_5$, $S(O)_nR^{13}$, $C_2$–$C_4$ alkylcarbonyl, $C_2$–$C_4$ alkoxycarbonyl, —$C(R^{10})$=N—$OR^{11}$ and —O— N=$C(R^{10})(R^{11})$; or $W^1$ is selected from the group $C_2$–$C_4$ alkenyl, $C_2$–$C_4$ alkynyl, O—$C_2$—$C_4$ alkenyl and O—$C_2$—$C_4$ alkynyl, each group optionally substituted with $R^9$;

n is 0, 1 or 2; and q is 0, 1, 2 or 3.

2. A compound according to claim 1 wherein:

A is a direct bond;

$R^1$ is selected from the group F and Cl in the 2-position; and $R^2$ is selected from the group H, F and Cl in the 6-position.

3. A compound according to claim 2 wherein:

$R^3$ is selected from the group $C_2$–$C_{10}$ alkenyl optionally substituted with at least one member independently selected from $R^9$; and $R^9$ is selected from the group phenyl and pyridyl, each optionally substituted with at least one member independently selected from W.

4. A compound according to claim 3 wherein:

Z is O;

$R^4$ and $R^5$ are H; and

W is selected from halogen, CN, and $OCHF_2$.

5. A compound according to claim 2 wherein:

$R^3$ is selected from the group $C_2$–$C_{10}$ alkynyl optionally substituted with at least one member independently selected from $R^9$; and $R^9$ is selected from the group phenyl and pyridyl, each optionally substituted with at least one member independently selected from W.

6. A compound according to claim 5 wherein:

Z is O;

$R^4$ and $R^5$ are H; and

W is selected from halogen, CN, and $OCHF_2$.

7. A compound according to claim 2 wherein:

$R^3$ is phenyl substituted with at least one member independently selected from $W^1$; and $W^1$ is selected from the group $C_2$–$C_4$ alkenyl and $C_2$–$C_4$ alkynyl, O—$C_2$—$C_4$ alkenyl and O—$C_2$—$C_4$ alkynyl, each group optionally substituted with $R^9$.

8. A compound according to claim 5 which is 2-(2,6-difluorophenyl)-4-[4-[(4-fluorophenyl)ethynyl]phenyl]-5,6-dihydro-4 H- 1,3 -oxazine.

9. An arthropodicidal composition comprising an arthropodicidally effective amount of a compound according to claim 1 and a carrier therefor.

10. A method for controlling arthropods comprising contacting the arthropods or their environment with an arthropodicidally effective amount of a compound according to claim 1.

* * * * *